(12) United States Patent
Tarabishy

(10) Patent No.: US 9,895,261 B1
(45) Date of Patent: Feb. 20, 2018

(54) DEVICE AND METHOD FOR TREATING RETINAL DETACHMENT

(71) Applicant: Ahmad Bakir Tarabishy, Tampa, FL (US)

(72) Inventor: Ahmad Bakir Tarabishy, Tampa, FL (US)

( * ) Notice: Subject to any disclaimer, the term of this patent is extended or adjusted under 35 U.S.C. 154(b) by 409 days.

(21) Appl. No.: 14/791,559

(22) Filed: Jul. 6, 2015

Related U.S. Application Data

(60) Provisional application No. 62/020,595, filed on Jul. 3, 2014.

(51) Int. Cl.
*A61M 5/00* (2006.01)
*A61F 9/007* (2006.01)
*A61M 27/00* (2006.01)
*A61M 1/00* (2006.01)

(52) U.S. Cl.
CPC ...... *A61F 9/00736* (2013.01); *A61F 9/00727* (2013.01); *A61M 1/008* (2013.01); *A61M 27/00* (2013.01)

(58) Field of Classification Search
CPC . A61F 9/00736; A61F 9/00727; A61M 1/008; A61M 27/00
See application file for complete search history.

(56) References Cited

U.S. PATENT DOCUMENTS

| 5,409,457 A * | 4/1995 | del Cerro | A61F 9/00736 604/117 |
| 2002/0133184 A1* | 9/2002 | LoRusso | A61F 9/00727 606/167 |
| 2012/0191064 A1* | 7/2012 | Conston | A61F 9/00727 604/506 |

OTHER PUBLICATIONS

Abdhish R. Bhavsar; Surgical Techniques in Ophthalmology Series: Retina and Vitreous Surgery; Chapter Two: Vitrectomy Surgery. Dec. 2008, pp. 15-50.

* cited by examiner

*Primary Examiner* — Philip R Wiest
(74) *Attorney, Agent, or Firm* — Michele L. Lawson; Smith & Hopen, P.A.

(57) ABSTRACT

A device, system and method for treating retinal detachment is presented. The device is generally comprised of a depressor, a cannula and a needle. In use, the depressor is used to create an indentation on the surface of the eye that can be viewed internally to determine the site for drainage. A cannula advancement mechanism is engaged and the cannula containing the needle is inserted into the determined drainage site. The needle is removed and an aspiration device is connected to the cannula to drain the subretinal fluid to treat retinal detachment.

18 Claims, 6 Drawing Sheets

DEVICE AND METHOD FOR TREATING RETINAL DETACHMENT

CROSS REFERENCE TO RELATED APPLICATION

This application is a nonprovisional of and claims priority to U.S. Provisional Patent Application No. 62/020,595, entitled "CANNULATED NEEDLE INTRODUCER TO DRAIN SUBRETINAL FLUID FOR TREATING RETINAL DETACHMENT," filed on Jul. 3, 2014 by the same inventor, the contents of which are hereby incorporated by reference.

FIELD OF THE INVENTION

This invention relates to a novel device and method for treating retinal detachment. More particularly, it relates to a device and method that allows direct visualization of the retina for drain placement and subretinal fluid drainage.

BACKGROUND OF THE INVENTION

Retinal detachment is a common cause of severe vision loss. In retinal detachment, the retina pulls away from the layer of blood cells which provide oxygen thus leaving the retinal cells lacking oxygen. Retinal detachment can occur when vitreous fluid leaks through a retinal hole or tear and collects underneath the retina. Tears or holes in the retina can occur for a number of reasons including disorders or aging that causes the retina to thin. A tear typically develops when there is a sudden collapse of the vitreous thus causing tugging on the retina with enough force to cause a tear. Fluid inside the vitreous may then travel through the tear and collect under the retina thus peeling it away from the underlying tissues which provide oxygen. In areas in which the retina is detached and the cells lack oxygen, vision may be lost if not treated quickly.

Rhegmatogenous retinal detachment is the most common etiology and is caused by a tear or hole that is usually in the peripheral retina.

Retinal detachment itself is painless, however symptoms are usually present before it occurs or advances. Symptoms of retinal detachment include the appearance of a large number of floaters; sudden flashes of light in the affected eye; and a shadow over a portion of the visual field that develops as the detachment progresses.

Several conditions may increase the chance of retinal detachment including nearsightedness; previous cataract surgery; eye trauma; previous retinal detachment in the other eye; family history of retinal detachment; or weak areas in the retina.

The principles of retinal detachment repair include identifying and treating the retinal breaks; draining the subretinal fluid; and internal or external tamponade of the breaks using scleral buckling or intravitreal gas or oil. Drainage of subretinal fluid is currently performed ab externo using an external sclerotomy, or ab interno using a drainage retinotomy. However, these techniques have significant disadvantages and complications. For example, external drainage with a sclerotomy requires an extensive dissection and cannot be done while directly visualizing the retina. External sclerotomy can also be complicated by hemorrhage, retinal incarceration, or iatrogenic retinal damage. Drainage retinotomy can be complicated by hemorrhage, recurrent detachment, or proliferative vitreoretinopathy. Internal drainage requires creating an iatrogenic retinal break.

Given the disadvantages in the current techniques for treating retinal detachment, what is needed is a device and system which would allow drainage site selection, drain placement and subretinal fluid drainage under direct visualization using an internal wide angle viewing system. Such a system would improve safety during drainage and avoid complications such as retinal incarceration and iatrogenic retinal breaks. A drainage retinotomy, which requires the creation of a posterior iatrogenic retinal break, can also be avoided.

SUMMARY OF INVENTION

A device for treating retinal detachment is presented comprising: a depressor having a proximal end, a distal end, a top portion and a bottom portion with the distal end terminating in a rounded knob; a cannula advancement mechanism positioned on the depressor; a cannula, positioned in the bottom portion of the depressor distally adjacent to the cannula advancement mechanism, and having an inner lumen, a proximal end and a distal end wherein distance between the proximal end and the distal end define a longitudinal distance of the cannula; and a needle positioned within the inner lumen of the cannula.

The distance between the proximal end and the distal end of the depressor defines a longitudinal distance of the depressor.

In some embodiments, the device may be further comprised of a longitudinal groove positioned in the bottom portion of the depressor. The cannula may be positioned within the longitudinal groove.

A longitudinal channel may also be present in the depressor with the cannula advancement mechanism being positioned within the longitudinal channel proximal to the longitudinal groove containing the cannula.

In some embodiments, the cannula advancement mechanism is a sliding mechanism having a flange at its distal end which is in contact with the proximal end of the cannula.

In some embodiments, the proximal end of the cannula may be adapted to receive a tube to an aspiration device. The cannula may taper inward from the proximal to the distal end so that diameter of the distal end is less than diameter of the proximal end. The cannula is manufactured of a soft material selected from the group consisting of plastics, rubbers and silicone.

A system for treating retinal detachment is also presented comprising: a depressor having a proximal end, a distal end, a top portion and a bottom portion with the distal end terminating in a rounded knob; a longitudinal groove positioned in the bottom portion of the depressor; a cannula advancement mechanism positioned on the depressor; a cannula, positioned in the bottom portion of the depressor distally adjacent to the cannula advancement mechanism, and having an inner lumen, a proximal end and a distal end wherein distance between the proximal end and the distal end define a longitudinal distance of the cannula; a needle positioned within the inner lumen of the cannula; and means for connecting the cannula to an aspiration device.

The cannula advancement mechanism may be a sliding mechanism. A longitudinal channel may also be present in the depressor with the sliding mechanism being positioned within the longitudinal channel proximal to the longitudinal groove containing the cannula. The sliding mechanism may have a flange at its distal end that is in contact with the proximal end of the cannula. The proximal end of the cannula may be adapted to receive a tube to an aspiration device.

The means for connecting the cannula to the aspiration device may be a flexible tube having opposing ends. The tube may be connected at one end to the proximal end of the cannula with the other end being connected to the aspiration device.

A method of treating retinal detachment comprising: providing a device for retinal detachment as described above; creating an indentation on the surface of the eye by gently pushing the knob of the depressor against the eye surface; selecting an appropriate drainage site; introducing the cannula containing the needle into the subretinal space by engaging the cannula advancement mechanism; removing the needle from the cannula; connecting the cannula to an aspiration device; draining the subretinal fluid from the eye using suction from the aspiration device; and removing the cannula from the eye once fluid is drained.

The proposed device facilitates precise placement of a subretinal drain under direct visualization and allows for surgeon controlled suction drainage of subretinal fluid. Subretinal fluid is drained in a carefully controlled fashion under direct visualization without needing to perform a drainage retinotomy, which some view as being unnecessarily traumatic to the retina. The proposed system and method of treating retinal detachment allows for drainage of subretinal fluid without requiring an extensive dissection that is needed for an external sclerotomy, or requiring creating an iatrogenic retinal break as is performed with a drainage retinotomy.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
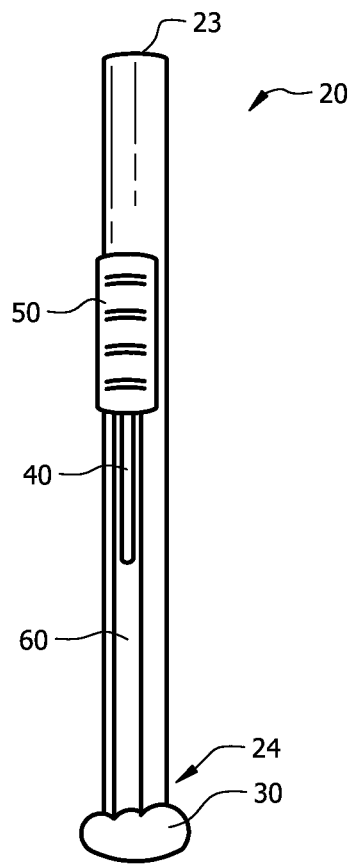
FIG. 1 is a perspective view of the depressor portion of the device illustrating the longitudinal groove and channel as well as the cannula advancement mechanism.

In the following detailed description of the preferred embodiments, reference is made to the accompanying drawings, which form a part hereof, and within which are shown by way of illustration specific embodiments by which the invention may be practiced. It is to be understood that there are other embodiments by which the invention may be practiced. It is to be understood that other embodiments may be utilized and structural changes may be made without departing from the scope of the invention.

Definitions

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose. Where particular values are described in the application and claims, unless otherwise stated, the term "about" meaning within an acceptable error range for the particular value should be assumed.

As used in the specification and claims, the singular form "a", "an" and "the" include plural references unless the context clearly dictates otherwise.

"Depressor" as used herein refers to an elongated shaft having proximal and distal ends. Distal end of depressor terminates in a bulbous knob. Depressor may be solid or may have a longitudinal groove into which a cannula may be positioned. Depressor may also, in some embodiments, have a longitudinal channel, the length of which cannula advancement mechanism may travel.

"Cannula advancement mechanism" as used herein refers to any mechanism which may be used to move cannula along the longitudinal axis of the depressor. In some embodiments, cannula advancement mechanism is a sliding mechanism, however other mechanisms are contemplated by the invention as long as they are capable of being used with the depressor and moving the cannula.

"Cannula" as used herein refers to a hollow tube having an inner lumen. In some embodiments, the cannula is tapered inwards from proximal to distal end so that the diameter of the distal end is smaller than the diameter of the proximal end. The cannula in some embodiments may contain a removable needle.

"Knob" as used herein refers to a bulbous, generally rounded protuberance that is present at the distal end of the depressor. The knob is used to make an indentation on the surface of the eye without rupturing the tissue. In some embodiments the knob is in a rounded ball-like shape.

"Channel" as used herein refers to a narrow trough or depression in the surface of the depressor which is sized to allow movement of the cannula advancement mechanism. At least a portion of the cannula advancement mechanism is positioned within the channel.

"Groove" as used herein refers to a trough in the surface of the depressor which is sized to fit a cannula.

"System" as used herein refers to the combination of the device including the depressor, the cannula and the needle as well as the tubing connecting the device to the aspiration device and the aspiration device itself.

The present invention provides a device, system and method of treating retinal detachment. The device is generally comprised of a depressor which is used to make an indentation on the surface of the eye and a removably attachable cannula containing a needle which is placed into the subretinal space and removably attached to an aspiration device such as a vacuum to evacuate the fluid in the subretinal space to treat retinal detachment.

As shown in FIGS. 1-4, device 10 is comprised of depressor 20 onto which cannula 70 is removably attached. Depressor 20 is an elongated shaft having anterior 21 and posterior 22 sides, proximal 23 and distal 24 ends, and top 25 and bottom 26 portions. Depressor can be between about 8 cm to about 20 cm in length. Distal end 24 terminates in bulbous knob 30. Knob 30 is generally of a rounded shape which enables it to make an indentation in the surface of the eye without causing damage to the surface of the eye. The diameter of knob can range from about 2 mm to about 6 mm.

As shown in FIG. 1, top portion 25 of anterior side 21 of depressor 20 may contain longitudinal channel 40. Longitudinal channel 40 may contain cannula advancement mechanism 50. In some embodiments, cannula advancement mechanism 50 may be a sliding mechanism. In some embodiments sliding mechanism 50 may have flange 55 which is positioned adjacent to proximal end 72 of cannula 70. In use, when sliding mechanism 50 is moved distally in the direction of cannula 70, flange 55 engages with and moves cannula 70 to advance cannula 70 towards distal end 24 of depressor 20 and subsequently into the exterior surface of the eye. Cannula advancement mechanism 50 may be retractable either manually, motorized, or electronically. While cannula advancement mechanism 50 is described herein as being a sliding mechanism, other cannula advancement mechanisms are contemplated by the invention including, but not limited to, a lever, a wheel system and a motorized system.

Figure 2:
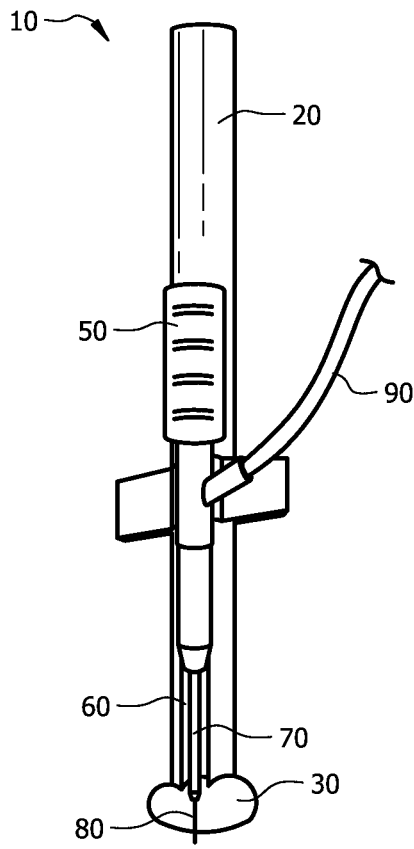
FIG. 2 is a perspective view of the depressor illustrating placement of the cannula in the groove of the depressor.
Figure 3:
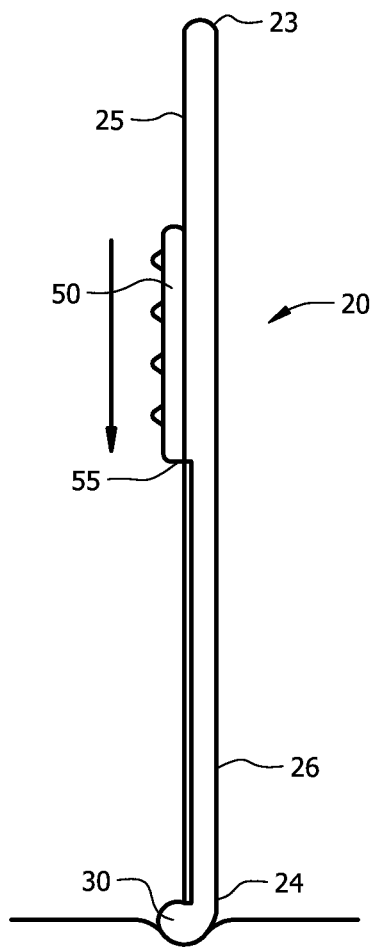
FIG. 3 is a side view of the device illustrating the depressor engaged on the surface of the eye to make an indentation. The cannula and cannula advancement mechanism is shown as being not yet in contact with the eye.
Figure 4:
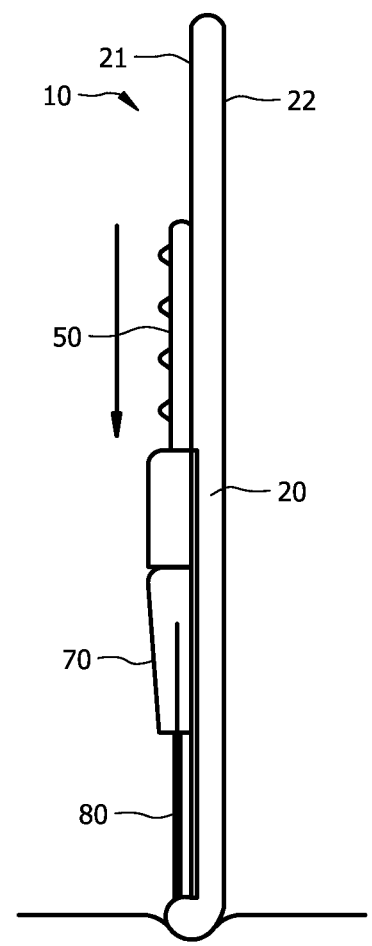
FIG. 4 is a side view of the device illustrating the engagement of the cannula and its positioning within the eye.

In some embodiments, depressor 20 may also have longitudinal groove 60 extending along anterior side 21 of bottom portion 26 of depressor 20. Longitudinal groove 60 is preferably positioned distally to longitudinal channel 40. Longitudinal groove 60 is sized to fit cannula 70 comfortably in width, length and depth. As shown in FIG. 2, cannula 70 is positioned within longitudinal groove 60 so that when cannula advancement mechanism 50 is not engaged with cannula 70, distal end 74 of cannula 70 does not extend past knob 30 of distal end 24 of depressor 20. Once the surgeon has determined the drainage site, cannula advancement mechanism 50 can be engaged with proximal end 72 of cannula 70 to advance cannula 70 out of longitudinal groove 60 and into the eye of the patient. As cannula 70 is advanced, distal end 74 of cannula 70 extends past knob 30 of distal end 24 of depressor 20 and into the eye of the patient.

Cannula 70 is an elongated hollow tube having proximal and distal ends and an inner lumen 76. Inner lumen 76 of cannula 70 houses needle 80 which passes through inner lumen 76 proximally to distally. Proximal end 72 of cannula 70 may be adapted for attachment of tubing 90 which allows attachment of cannula 70 to aspiration device such as a vacuum or other suction device. This attachment for tubing 90 may occur in a number of ways including, but not limited to, Luer locks, male and female threads, etc.

Figure 5:
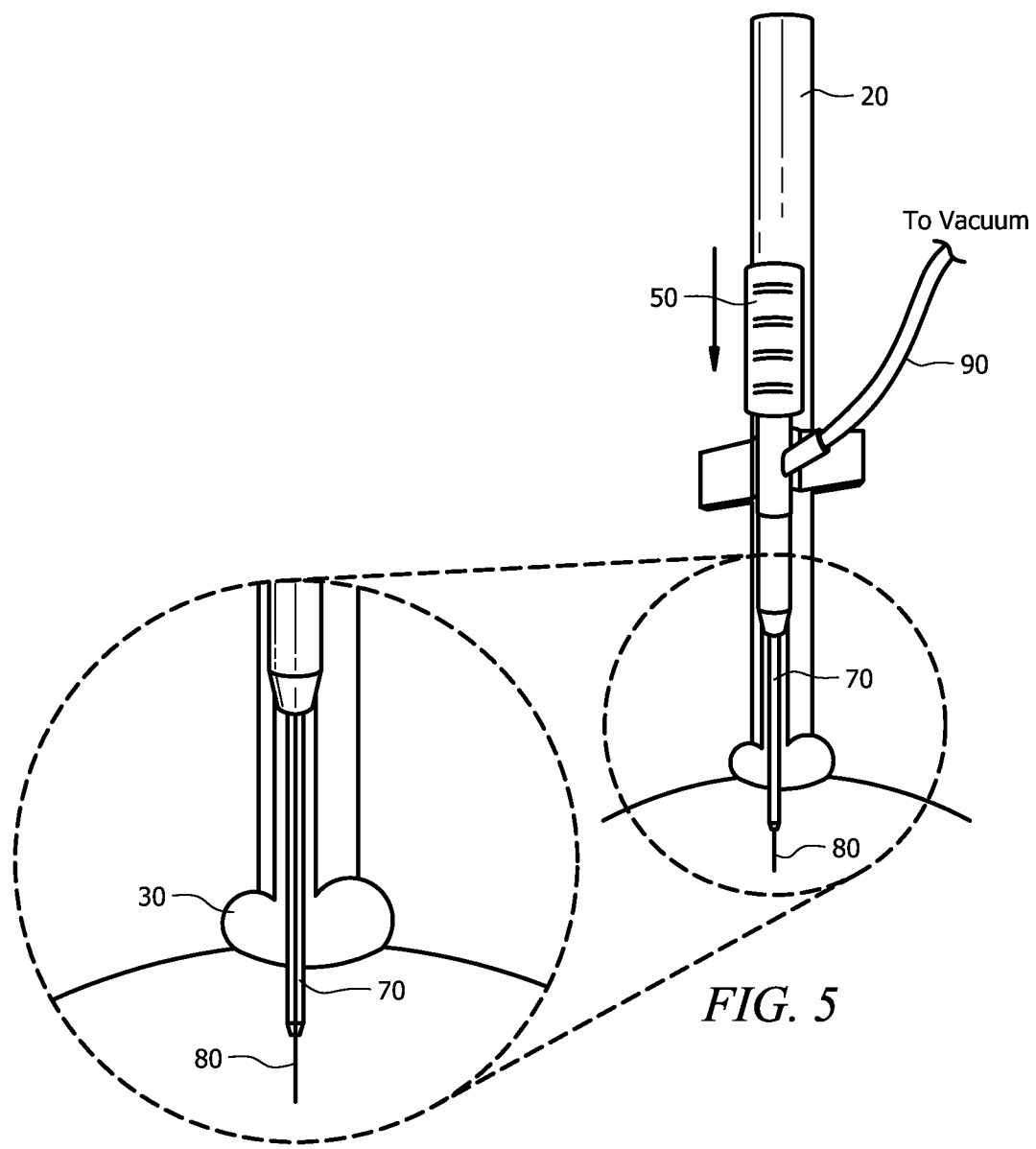
FIG. 5 is a front view of the device showing the depressor creating an indentation on the eye surface and the cannula and needle entering the eye.
Figure 6:
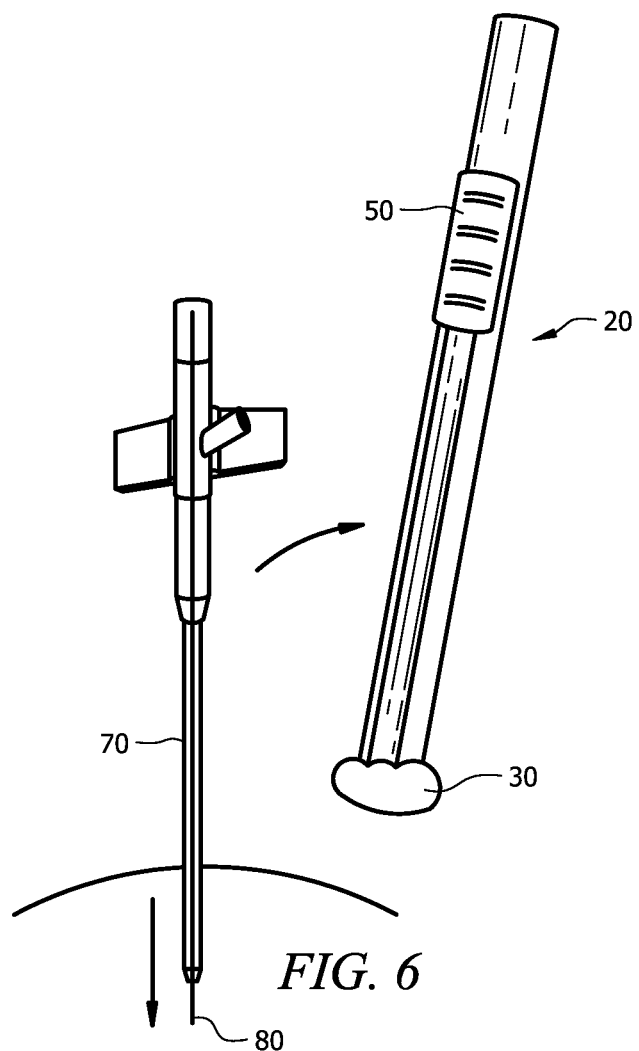
FIG. 6 is a front view of the device showing the depressor being removed from the cannula. Once the depressor is removed, the cannula stays in position in the eye.
Figure 7:
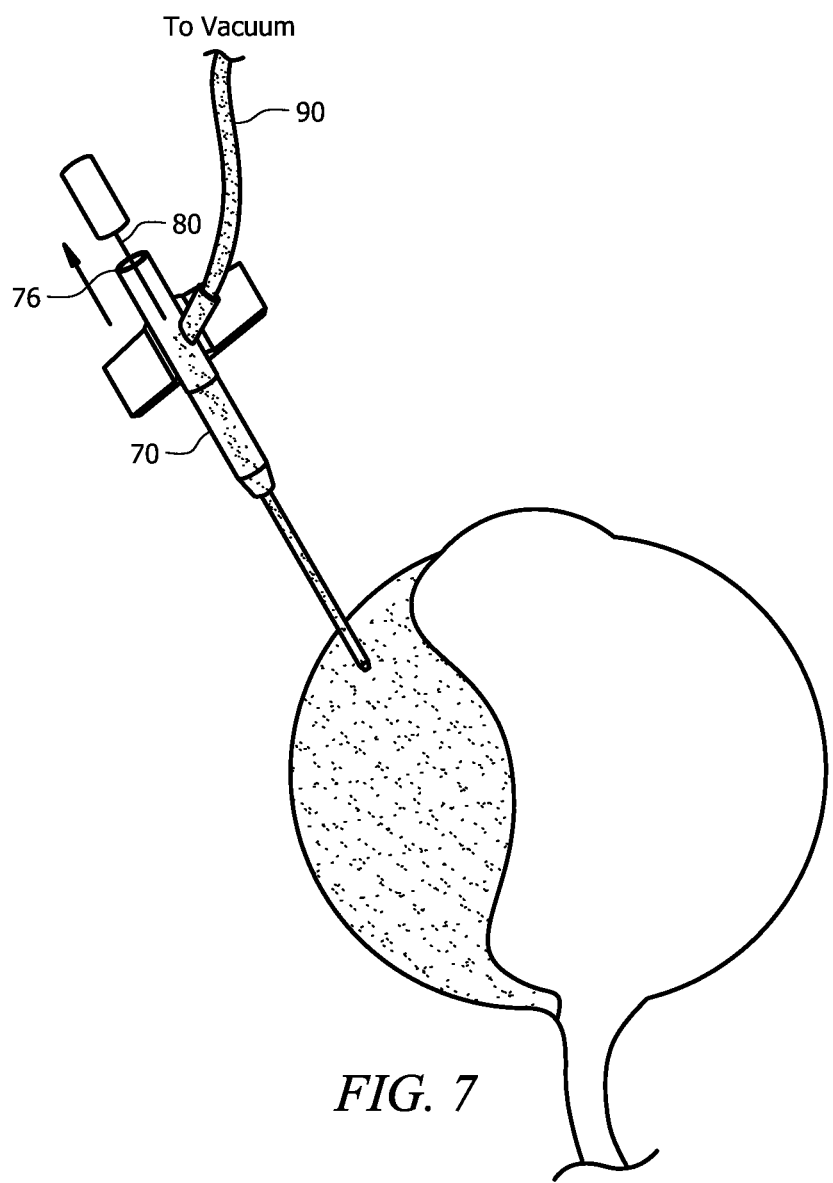
FIG. 7 is a perspective view of the needle of the device being removed from the cannula. As shown in the image, the cannula stays in position in the eye after the needle is removed.

Cannula 70 may gradually taper inwards from proximal end 72 to distal end 74 so that distal end 74 has a significantly smaller diameter than proximal end 72 of cannula 70. When cannula 70 is advanced towards the surface of the eye, needle 80 may protrude from distal end 74 of cannula 70 to break the surface of the sclera and allow cannula 70 to become positioned within the eye. (FIG. 5) Once cannula 70 is positioned in the eye, depressor 20 may be removed. (FIG. 6) Cannula 70 is relatively self-retaining, being held in place by the sclera, but is also easily removed once the procedure is complete. Once depressor 20 is removed, needle 80 may also be removed so that fluid can be aspirated. (FIG. 7)

In some embodiments, cannula 70 may be a commercially available cannula, such as an intravenous cannula or a simple cannula, while in other embodiments, cannula is custom made to fit depressor 20.

Depressor 20 may be manufactured of a hard, medical grade material including, but not limited to, a metal such as stainless steel, hard plastics, etc.

Cannula 70 may be manufactured of a soft, medical grade material, including but not limited to, soft plastics, rubbers, and silicone.

Figure 8:
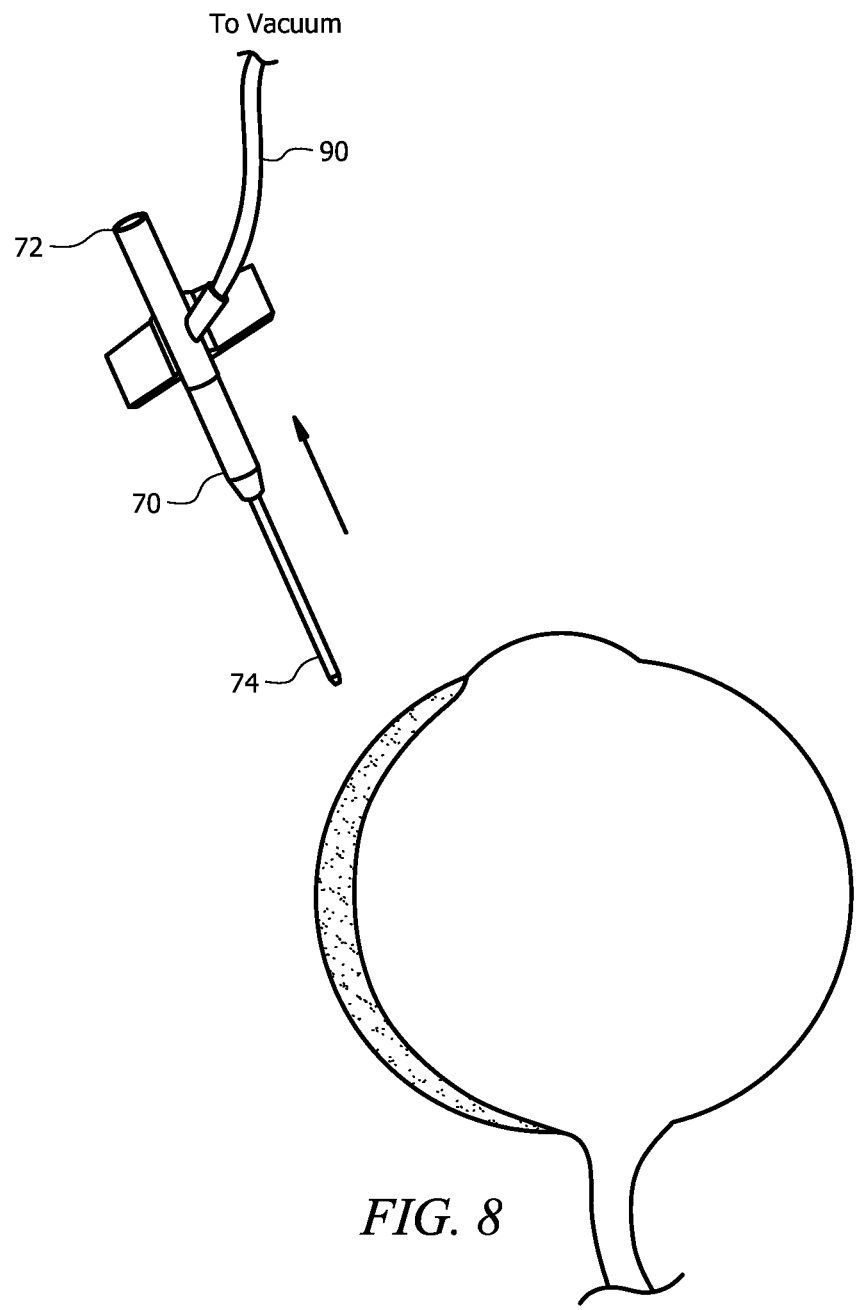
FIG. 8 is a perspective view of the cannula being removed from the device after suction is completed.

In use, knob 30 of depressor 20 is positioned on the outer surface of the sclera of the eye and gently pressed against the surface to cause an indentation in the sclera that can be seen internally by the surgeon. (FIG. 3) This allows the surgeon to determine an appropriate external drainage site. Once the external drainage site is determined, cannula advancement mechanism 50 is employed to advance cannula 70, and needle 80, through the sclera and into the subretinal space. (FIGS. 4 and 5) Depressor 20 may then be moved away from cannula 70 and thus the surface of the eye. (FIG. 6) Once an appropriate depth is determined, needle 80 may be removed from cannula 70 so that only cannula 70 is left within the eye. (FIG. 7) One end of hose 90 may be attached to proximal end 72 of cannula 70 with the other end being attached to an aspiration device such as a vacuum to aspirate fluid from the subretinal space. Once all fluid is drained from the subretinal space, cannula 70 may be removed from the eye. (FIG. 8)

Aspiration device may take many forms such as a hand operated suction device, a foot pedal operated suction device, etc. Many different aspiration devices are contemplated by the invention as long as they are capable of connecting to cannula and removing fluid from the eye.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween. Now that the invention has been described,

What is claimed is:

1. A device for treating retinal detachment comprising:
   a depressor having a proximal end, a distal end, a top portion and a bottom portion wherein distance between the proximal end and the distal end define a longitudinal distance of the depressor wherein the distal end terminates in a rounded knob;
   a cannula advancement mechanism positioned on the depressor;
   a cannula, positioned in the bottom portion of the depressor distally adjacent to the cannula advancement mechanism, and having an inner lumen, a proximal end and a distal end wherein distance between the proximal end and the distal end define a longitudinal distance of the cannula;
   a longitudinal groove in the bottom portion of the depressor wherein the cannula is positioned within the longitudinal groove;
   a longitudinal channel in the depressor wherein the cannula advancement mechanism is positioned within the longitudinal channel proximal to the longitudinal groove containing the cannula; and
   a needle positioned within the inner lumen of the cannula.

2. The device of claim 1, wherein the cannula advancement mechanism is a sliding mechanism.

3. The device of claim 2, wherein the sliding mechanism has a flange at its distal end wherein the flange of the sliding mechanism is in contact with the proximal end of the cannula.

4. The device of claim 2, further comprising a longitudinal channel in the depressor wherein the sliding mechanism is positioned within the longitudinal channel proximal to the cannula.

5. The device of claim 1, wherein the proximal end of the cannula is adapted to receive a tube to an aspiration device.

6. The device of claim 1, wherein the cannula tapers inward from the proximal to the distal end so that diameter of the distal end is less than diameter of the proximal end.

7. The device of claim 1, wherein the cannula is manufactured of a soft material selected from the group consisting of plastics, rubbers and silicone.

8. A system for treating retinal detachment comprising:
   a depressor having a proximal end, a distal end, a top portion and a bottom portion wherein distance between the proximal end and the distal end define a longitudinal distance of the depressor wherein the distal end terminates in a rounded knob;
   a longitudinal groove positioned in the bottom portion of the depressor;
   a cannula advancement mechanism positioned on the depressor;
   a cannula, positioned within the longitudinal groove and distally adjacent to the cannula advancement mechanism, having an inner lumen, a proximal end and a distal end wherein distance between the proximal end and the distal end define a longitudinal distance of the cannula;
   a needle positioned within the inner lumen of the cannula; and
   means for connecting the cannula to an aspiration device.

9. The system of claim 8, wherein the cannula advancement mechanism is a sliding mechanism.

10. The system of claim 9, further comprising a longitudinal channel in the depressor wherein the sliding mechanism is positioned within the longitudinal channel proximal to the longitudinal groove containing the cannula.

11. The system of claim 9, wherein the sliding mechanism has a flange at its distal end wherein the flange of the sliding mechanism is in contact with the proximal end of the cannula.

12. The system of claim 8, wherein the proximal end of the cannula is adapted to receive a tube to an aspiration device.

13. The system of claim 12, wherein the means for connecting the cannula to the aspiration device is a flexible tube having opposing ends wherein the tube is connected at one end to the proximal end of the cannula and the other end is connected to the aspiration device.

14. A method of treating retinal detachment comprising:
   providing a device for retinal detachment comprising:
      a depressor having a proximal end, a distal end, a top portion and a bottom portion wherein distance between the proximal end and the distal end define a longitudinal distance of the depressor wherein the distal end terminates in a rounded knob;
      a cannula advancement mechanism positioned on the depressor;
      a cannula, positioned distally adjacent to the cannula advancement mechanism, and having an inner lumen, a proximal end and a distal end wherein distance between the proximal end and the distal end define a longitudinal distance of the cannula; and
      a needle positioned within the inner lumen of the cannula;
   creating an indentation on the surface of the eye by gently pushing the knob of the depressor against the eye surface;
   selecting an appropriate drainage site;
   introducing the cannula containing the needle into the subretinal space by engaging the cannula advancement mechanism;
   removing the needle from the cannula;
   connecting the cannula to an aspiration device;
   draining the subretinal fluid from the eye using suction from the aspiration device; and
   removing the cannula from the eye once fluid is drained;
   wherein drainage of the subretinal fluid allows retina to reattach to choroid.

15. The method of claim 14, wherein the cannula advancement mechanism is a sliding mechanism.

16. The method of claim 15, further comprising a longitudinal groove in the bottom portion of the depressor wherein the cannula is positioned within the longitudinal groove.

17. The method of claim 16, further comprising a longitudinal channel in the depressor wherein the sliding mechanism is positioned within the longitudinal channel proximal to the longitudinal groove containing the cannula.

18. The method of claim 14, wherein the cannula is connected to the aspiration device by a flexible tube having opposing ends wherein the tube is connected at one end to the proximal end of the cannula and the other end is connected to the aspiration device.

* * * * *